(12) United States Patent
Kishimoto et al.

(10) Patent No.: US 8,684,939 B2
(45) Date of Patent: Apr. 1, 2014

(54) BLOOD PRESSURE MEASUREMENT DEVICE

(75) Inventors: Hiroshi Kishimoto, Kyoto (JP); Yuuichiro Tamaki, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 430 days.

(21) Appl. No.: 13/033,788

(22) Filed: Feb. 24, 2011

(65) Prior Publication Data

US 2011/0144506 A1   Jun. 16, 2011

Related U.S. Application Data

(63) Continuation of application No. PCT/JP2009/064164, filed on Aug. 11, 2009.

(30) Foreign Application Priority Data

Sep. 2, 2008   (JP) ................................. 2008-225096

(51) Int. Cl.
*A61B 5/02* (2006.01)
(52) U.S. Cl.
USPC ............................ 600/490; 600/485; 600/500
(58) Field of Classification Search
USPC .......................... 600/485, 490, 491, 493, 499
See application file for complete search history.

(56) References Cited

U.S. PATENT DOCUMENTS

| | | | |
|---|---|---|---|
| 2006/0047206 A1* | 3/2006 | Sano et al. .................... | 600/490 |
| 2007/0038133 A1* | 2/2007 | Kishimoto et al. ............ | 600/490 |
| 2009/0312651 A1* | 12/2009 | Sano et al. .................... | 600/493 |

FOREIGN PATENT DOCUMENTS

| | | |
|---|---|---|
| JP | 2005-334049 | 12/2005 |
| JP | 2006-234426 | 9/2006 |
| JP | 2007-132822 | 5/2007 |

OTHER PUBLICATIONS

Patent Abstracts of Japan for Japanese Publication No. 2005-334049, Publication date Dec. 8, 2005 (1 page).
Patent Abstracts of Japan for Japanese Publication No. 2006-234426, Publication date Sep. 7, 2006 (1 page).
Patent Abstracts of Japan for Japanese Publication No. 2007-132822, Publication date May 31, 2007 (1 page).
International Search Report for International Application No. PCT/JP2009/064164, mailed on Sep. 8, 2009 (2 pages).

* cited by examiner

*Primary Examiner* — Navin Natnithithadha
*Assistant Examiner* — Etsub Berhanu
(74) *Attorney, Agent, or Firm* — Osha Liang LLP

(57) ABSTRACT

A blood pressure measurement device is mounted with a radio-controlled clock function in a main body without lowering reception performance of the standard radio wave of the radio-controlled clock. A substrate including a sensor mounting surface and a sensor non-mounting surface is mounted with a pressure sensor. An antenna for receiving the standard radio wave including time information of the radio-controlled clock is mounted. The antenna includes a bar-shaped magnetic body core and a coil wound around the magnetic body core. A pump is arranged such that an axis line direction of the motor and an extending direction of the magnetic body core are substantially orthogonal. The substrate and the substrate are arranged so that the sensor non-mounting surface of the substrate and the antenna mounting surface of the sensor face each other.

6 Claims, 19 Drawing Sheets

BLOOD PRESSURE MEASUREMENT DEVICE

TECHNICAL FIELD

The present invention relates to blood pressure measurement devices, and in particular, to a blood pressure measurement device mounted with a radio-controlled clock.

BACKGROUND ART

Recently, the use of a blood pressure measurement device in homes and the like is widely spreading for the purpose of early detection of lifestyle related diseases caused by high blood pressure and blood pressure management. The blood pressure is one index for analyzing the heart function, where performing risk analysis based on the blood pressure is effective in preventing cerebrovascular diseases such as brain hemorrhage and brain infarct, and vascular diseases such as cardio arrest and cardio infarct.

The blood pressure changes by reaction to individual body activity and stress, as well as the cardiovascular back action to a behavior pattern, where the blood pressure has a daily fluctuation rhythm of lowering during sleep and rising before and after waking. For example, the sudden rise in blood pressure that occurs between one hour and one and a half hour after waking up called a morning surge has a causal connection with apoplexy, and the mutual relationship with the change in blood pressure needs to be grasped to perform the risk analysis of the cardiovascular disease. With increasing importance on the blood pressure management, the importance of setting the clock of the blood pressure measurement device to specify when a measurer measured the blood pressure is increasing.

Consideration is made in mounting a radio-controlled clock to the blood pressure measurement device as means for facilitating clock setting of the blood pressure measurement device. The radio-controlled clock is a clock having a function of receiving a standard radio wave and automatically correcting an error of the display time to display an accurate time. In the radio-controlled clock, the built-in receiver reads the standard radio wave every fixed time and automatically sets the time. Thus, the trouble of manually setting the time can be omitted and an accurate time in units of seconds can be known as long as the radio-controlled clock is in an environment capable of normally receiving the radio wave.

Metal objects such as a motor for driving a pump, a metal body for protecting a pressure sensor, and a valve for depressurizing the cuff and adjusting the cuff pressure exist inside the blood pressure measurement device. Upon mounting a reception function of the standard radio wave of the radio-controlled clock inside a main body of the blood pressure measurement device, reception performance may lower due to an adverse effect of the metal objects depending on the mounting method. Since an error occurs in time and reliability lowers if the reception performance lowers, preventing the lowering of the reception performance is desired. Various techniques for preventing the lowering of the reception performance of the standard radio wave in the radio-controlled clock have been conventionally proposed (see e.g., Japanese Unexamined Patent Publication No. 2007-132822 (Patent Document 1) and Japanese Unexamined Patent Publication No. 2006-234426 (Patent Document 2)).

Patent Document 1: Japanese Unexamined Patent Publication No. 2007-132822
Patent Document 2: Japanese Unexamined Patent Publication No. 2006-234426

SUMMARY OF INVENTION

In the technique described in Patent Document 1, various considerations are made on the method of arranging an antenna and a plurality of motors, but consideration is not made on the method of arranging the antenna with respect to a metal surface. Therefore, if a directivity surface of the antenna is arranged parallel to the metal surface, the reception sensitivity may lower. In the technique described in Patent Document 2, directional characteristics improve if a configuration of adjusting the tilt of the antenna in the core axis direction is adopted, but the configuration becomes complicated and the number of components and the unit price increase.

Therefore, one or more embodiments of the present invention provides a blood pressure measurement device realizing a configuration of mounting the radio-controlled clock function in the main body of the blood pressure measurement device without lowering the reception performance of the standard radio wave of the radio-controlled clock.

A blood pressure measurement device according to one or more embodiments of the present invention includes a cuff, a pump, a flow rate control valve, a pressure sensor, a first substrate, a radio-controlled clock, and a second substrate. The cuff is attached to a blood pressure measurement site of a person to be measured. The cuff includes a gas bag filled with gas. The pump transfers gas to the gas bag. The flow rate control valve controls the gas flow rate discharged from the gas bag. The pressure sensor detects pressure in the gas bag. The first substrate includes a sensor mounting surface and a sensor non-mounting surface, which is a back surface of the sensor mounting surface. The pressure sensor is mounted on the sensor mounting surface. The radio-controlled clock includes an antenna for receiving a standard radio wave including time information, and times a current time. The second substrate includes an antenna mounting surface and an antenna non-mounting surface, which is a back surface of the antenna mounting surface. The antenna is mounted on the antenna mounting surface. The pump includes a motor. The motor rotates about an axis line and operates the pump. The antenna includes a bar-shaped magnetic body core and a coil wound around the magnetic body core. The pump is arranged such that an axis line direction of the motor and an extending direction of the magnetic body core are substantially orthogonal. The first substrate and the second substrate are arranged so that the sensor non-mounting surface of the first substrate and the antenna mounting surface of the second substrate face each other, or so that the sensor mounting surface of the first substrate and the antenna non-mounting surface of the second substrate face each other.

According to one or more embodiments of the present invention, the pump is arranged such that an axis line direction of the motor and an extending direction of the magnetic body core are orthogonal, that is, the two directions intersect forming an angle of 90°, allowing the effect of not lowering the reception performance of the standard radio wave of the radio-controlled clock to be more efficiently obtained. However, the effect of not lowering the reception performance of the standard radio wave of the radio-controlled clock can be similarly obtained even if the angle formed by the axis line direction of the motor and the extending direction of the magnetic body core is not strictly 90° and is an angle slightly deviated from 90°. That is, "substantially orthogonal" includes a case where the axis line direction of the motor and the extending direction of the magnetic body core intersect forming the angle of 90° and also includes a case where the axis line direction of the motor and the extending direction of the magnetic body core intersect to form not 90° but an angle close to 90°. For example, according to one or more embodiments of the present invention, the axis line direction of the motor and the extending direction of the magnetic body core intersect to form an angle in a range of greater than or equal to 80° and smaller than or equal to 100°, or intersect to form an angle in a range of greater than or equal to 85° and smaller than or equal to 95°.

According to one or more embodiments of the blood pressure measurement device, the second substrate is arranged parallel to the installing surface where the blood pressure measurement device is installed. In this case, the second substrate may be arranged strictly parallel to the installation surface (i.e., angle formed by the second substrate and the installation surface is 0°). "Arranging in parallel" also includes a case where the second substrate and the installation surface are arranged not strictly parallel but are arranged to become close to parallel. For example, the second substrate and the installation surface are arranged so that the angle is in the range of greater than or equal to 0° and smaller than or equal to 10°, or arranged so that the angle is in the range of greater than or equal to 0° and smaller than or equal to 5°.

In the blood pressure measurement device, the first substrate may be arranged inclined with respect to the second substrate. The first substrate and the second substrate may be arranged in parallel.

The flow rate control valve is an electromagnetic drive valve, and the blood pressure measurement device may be arranged such that a direction of a magnetic field generated by the electromagnetic drive valve and the extending direction of the magnetic body core are orthogonal.

The second substrate is interposed between the flow rate control valve and the antenna, and the flow rate control valve may be installed so that the antenna non-mounting surface of the second substrate and the flow rate control valve face each other.

According to one or more embodiments of the present invention, the lowering of the reception performance of the standard radio wave of the radio-controlled clock mounted in the main body of the blood pressure measurement device can be suppressed.

DETAILED DESCRIPTION OF THE INVENTION

Figure 1:
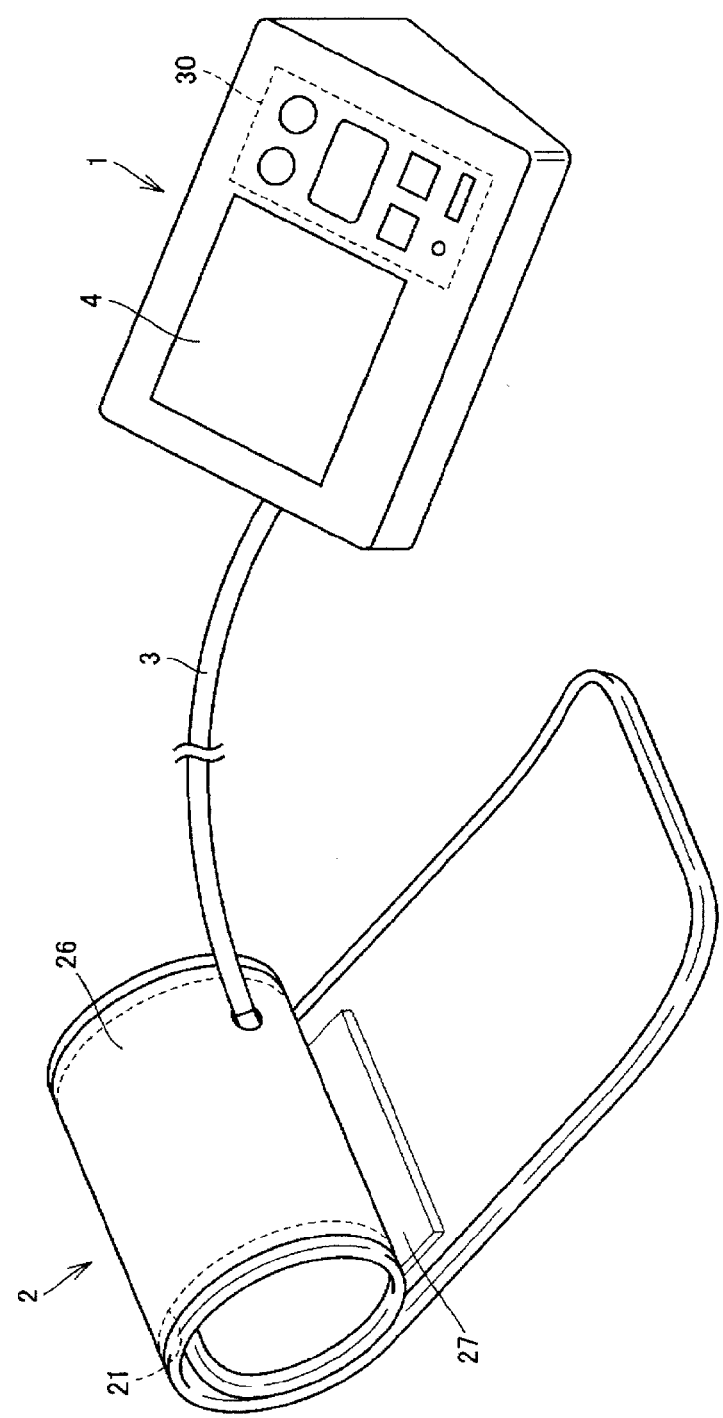
FIG. 1 is an overall perspective view showing an outer appearance of a blood pressure measurement device.

Embodiments of the present invention will be hereinafter described based on the drawings. In the following drawings, same reference numerals are denoted for the same or corresponding portions, and the description thereof will not be repeated.

In the embodiments described below, each configuring element is not necessarily essential in the present invention unless particularly stated. When referring to numbers, amounts, and the like in the following embodiments, the numbers and the like are illustrative unless particularly stated, and the scope of the invention is not necessarily limited by the number, the amount, and the like.

First Embodiment

Figure 2:
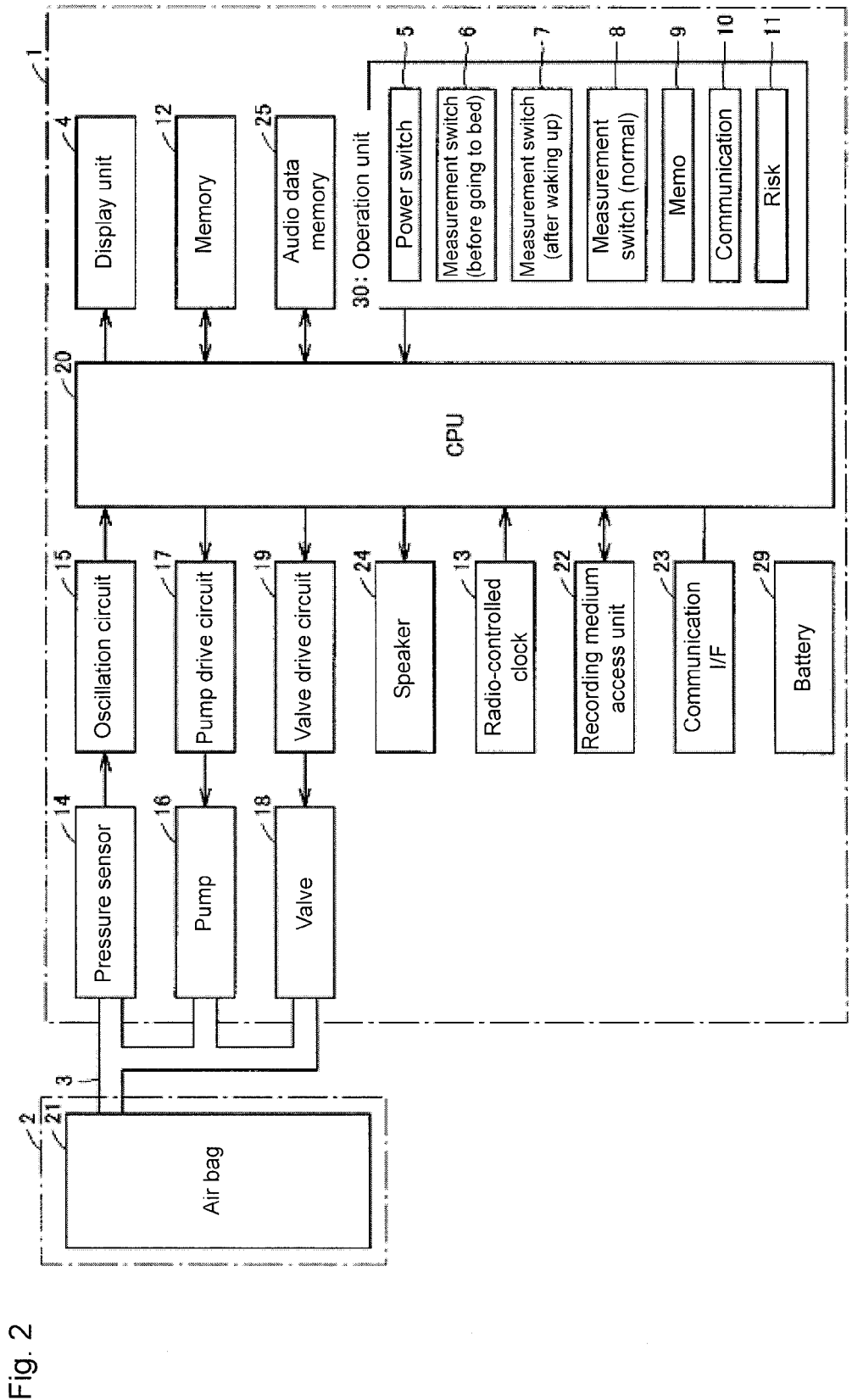
FIG. 2 is a block diagram showing an outline of an internal configuration of the blood pressure measurement device.

FIG. 1 is an overall perspective view showing an outer appearance of a blood pressure measurement device. FIG. 2 is a block diagram showing an outline of an internal configuration of the blood pressure measurement device. A schematic configuration of a home use blood pressure measurement device (hereinafter also simply referred to as a sphygmomanometer) will be described with reference to FIG. 1 and FIG. 2. The sphygmomanometer according to one or more embodiments of the present invention includes a main body 1 incorporating a control device for the blood pressure measurement, a cuff 2 to be attached to a blood pressure measurement site of a person to be measured to pressurize a blood pressure measurement site by air pressure, and an air tube 3 for coupling the main body 1 and the cuff 2.

As shown in FIG. 1, the main body 1 includes on an outer surface a display unit 4 arranged so that the person to be measured can check the display content, and an operation unit 30 arranged so that the person to be measured can operate from the outside. The cuff 2 includes an air bag 21 for compression that is filled and accumulated with air sent out from the main body 1 and transferred through the air tube 3 and that is used to compress the artery of the measurement site (upper arm). The cuff 2 has the compression air bag 21 arranged on an inner surface side, and includes a band-shaped band 26 for attaching to the measurement site (upper arm) and a surface fastener 27 for wrapping and fixing the band 26 around the upper arm.

As shown in FIG. 2, the main body 1 includes a pressure sensor 14 serving as a pressure detection unit for detecting the pressure in the air bag 21, and an oscillation circuit 15. The pressure sensor 14 outputs the change in pulse pressure of the site to be measured detected with the air bag 21 incorporated in the cuff 2 as a signal of a pulse wave. The oscillation circuit 15 outputs a pulse signal of a cycle that complies with a voltage signal indicating the pulse wave signal outputted from the pressure sensor 14. The main body 1 also includes a pump 16 and a valve 18 for adjusting a pressurization (air pressure) level by the air bag 21, a pump drive circuit 17 for driving the pump 16 and a valve drive circuit 19 for adjusting opening and closing of the valve 18. The pump 16 serving as an air pump transfers gas (air) to the air bag 21. The valve 18 serving as a flow rate control valve controls the flow rate of the gas discharged from the air bag 21.

The main body 1 further includes the display unit 4, a memory 12, the operation unit 30, a radio-controlled clock 13 for performing the timing operation and outputting timing data, a recording medium access unit 22, a communication I/F (abbreviation for interface) 23, a speaker 24, an audio data memory 25 and a battery 29, as well as a CPU (Central Processing Unit) 20 for controlling each of these units. The CPU 20 calculates the blood pressure value, the number of pulses, and the like of the person to be measured based on the pulse signal inputted from the oscillation circuit 15. The air bag 21, the pressure sensor 14, the pump 16, and the valve 18 are connected by the air tube 3. A power supply for driving, which is supplied to each unit arranged in the main body 1, may be supplied from a commercial power supply instead of the battery 29.

The operation unit 30 includes a power switch 5, measurement switches 6, 7, and 8, a memo switch 9, a communication switch 10, and a risk display switch 11. The power switch 5 is operated to turn ON/OFF the power supply of the main body 1. Each measurement switch 6, 7, 8 is operated to instruct the start of the blood pressure measurement. The measurement switch 6 is operated when the blood pressure measurement is carried out before going to bed such as within one hour before going to bed, and similarly, the measurement switch 7 is operated when the blood pressure measurement is carried out after waking up such as within one hour after waking up, and the measurement switch 8 is operated when the blood pressure measurement is carried out in other time bands.

The memo switch 9 is operated when the blood pressure measurement is carried out under a special situation. For example, the person to be measured operates the memo switch 9 when forgetting to take a medicine and carrying out the blood pressure measurement although instructed by a doctor to carry out the blood pressure measurement after taking the prescribed medicine. In this case, information indicating that it is the blood pressure measurement result of a case in which the medicine is not taken is added to the blood pressure measurement result by operating the memo switch 9, and the blood pressure measurement result is recorded in the memory 12. The communication switch 10 is operated when transmitting the result data measured by the main body 1 to an external device through communication. The risk display switch 11 is operated to display the information on cardiovascular risks based on the measurement result data by the main body 1 on the display unit 4.

The recording medium access unit 22 reads data from a recording medium or writes data to the recording medium attached to a recording medium attachment portion (not shown) formed in the main body 1 under the control of the CPU 20. The communication I/F 23 communicates with the external device through a cable under the control of the CPU 20. The memory 12 stores the measurement result data, and various types of programs and data for controlling the blood pressure measurement operation, the display operation by the display unit 4, the communication operation, and the like.

When measuring the blood pressure of the person to be measured in the sphygmomanometer configured as above, the cuff 2 is attached to the blood pressure measurement site (upper arm) of the person to be measured. The valve 18 is closed under the control of the CPU 20 so that all the air discharged from the pump 16 flows out to the air bag 21 thereby pressurizing the air bag 21. The valve 18 is opened to discharge the air in the air bag 21 to the outside through the valve 18 thereby depressurizing the air bag 21. In this case, the CPU 20 converts the pulse signal (pressure signal) outputted from the oscillation circuit 15 to digital data, and then applies a predetermined algorithm to the relevant data to determine the systolic blood pressure and the diastolic blood pressure and to calculate the number of pulses.

Figure 3:
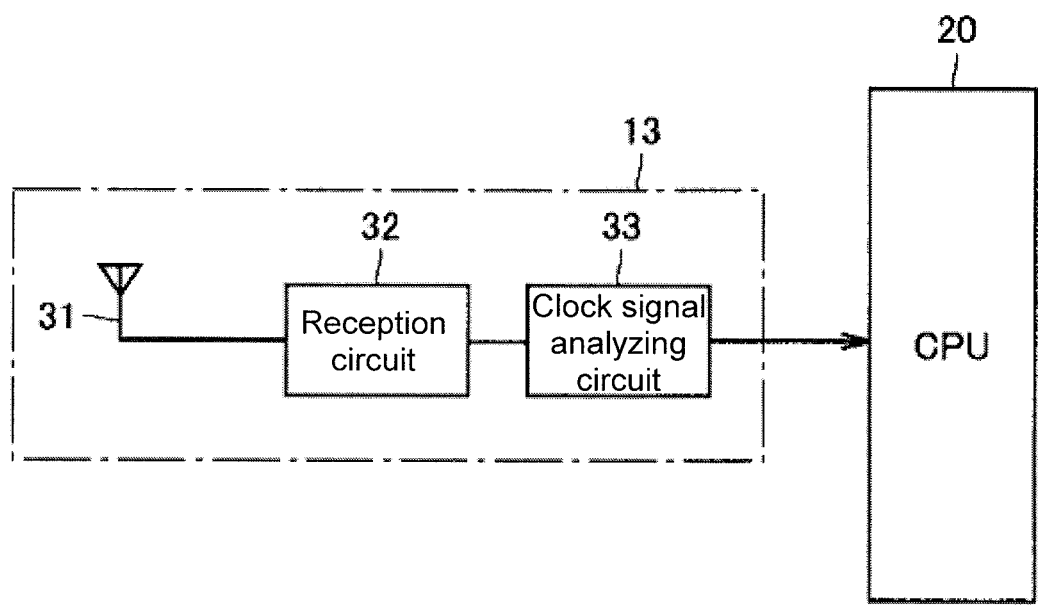
FIG. 3 is a block diagram showing a schematic configuration of a radio-controlled clock.

FIG. 3 is a block diagram showing a schematic configuration of the radio-controlled clock. As shown in FIG. 3, the radio-controlled clock 13 mounted inside the main body 1 includes an antenna 31, a reception circuit 32, and a clock signal analyzing circuit 33. When a radio wave reception command is inputted every predetermined time or from the outside, the CPU 20 controls the reception circuit 32 and the clock signal analyzing circuit 33 to have the antenna 31 receive a standard radio wave of a predetermined frequency including time information (e.g., long wave represented by JJY standard radio wave of 40 kHz or 60 kHz).

The reception circuit 32 cuts an unnecessary component from the reception signal of the standard radio wave received by the antenna 31, and extracts the target frequency signal. The clock signal analyzing circuit 33 counts the frequency signals extracted by the reception circuit 32 to time the accurate current time. The data of such current time is transmitted to the CPU 20 and displayed on the display unit 4, and the measurement time is added to the blood pressure measurement result and recorded in the memory 12 when the person to be measured has measured the blood pressure.

Figure 4:
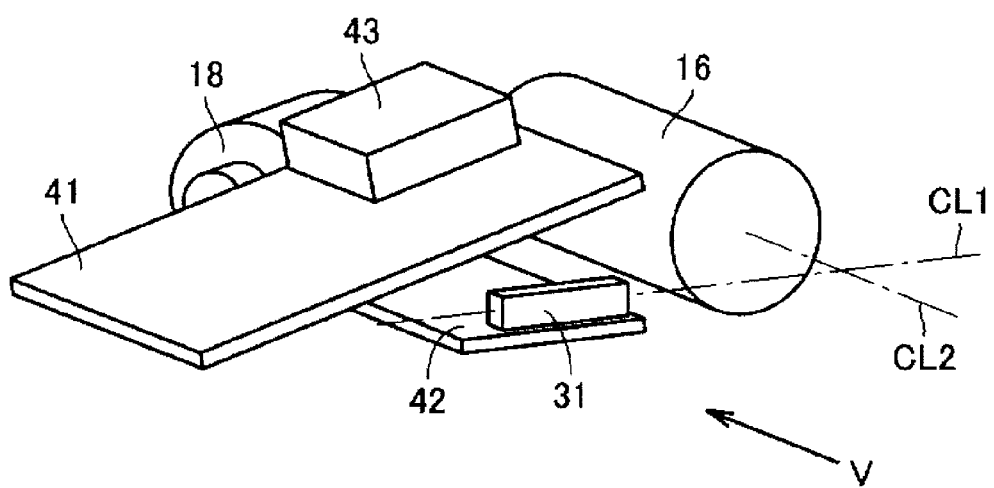
FIG. 4 is a perspective view showing an arrangement of each device mounted in a main body of the sphygmomanometer.
Figure 5:
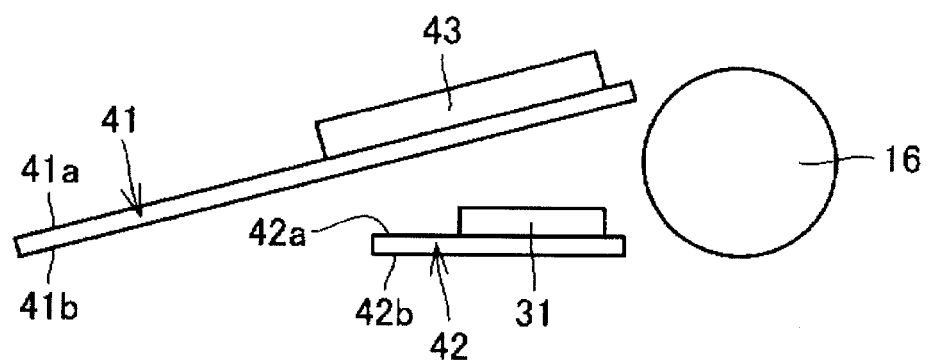
FIG. 5 is a side view of each device shown in FIG. 4 seen from a direction of an arrow V in FIG. 4.

FIG. 4 is a perspective view showing an arrangement of each device mounted in the main body of the sphygmomanometer. FIG. 5 is a side view of each device shown in FIG. 4 seen from a direction of an arrow V in FIG. 4. As shown in FIG. 4 and FIG. 5, a substrate 41 serving as a first substrate, a substrate 42 serving as a second substrate, and the pump 16 are installed inside the main body 1 of the sphygmomanometer. The substrate 41 and the substrate 42 are arranged inside the main body 1 as separate substrates different from each other.

The pressure sensor 14 shown in FIG. 2 is mounted on the substrate 41. The pressure sensor 14 is a well-known capacitance sensor, and has its periphery covered by a metal shield case 43. The pressure sensor 14 is likely to be subjected to the influence of electromagnetic wave generated from surrounding devices, and thus the shield case 43 is arranged at the periphery of the pressure sensor 14 as an electromagnetic shield and in an aim of mechanically protecting the pressure sensor 14. The antenna 31 configuring one component of the radio-controlled clock 13 is mounted on the substrate 42.

The pressure sensor 14 and the shield case 43 are mounted on a sensor mounting surface 41$a$ that is a surface on one side of a flat plate-shaped substrate 41. The sensor mounting surface 41$a$ and a sensor non-mounting surface 41$b$, which is a surface on the other side of the substrate 41 opposite to the sensor mounting surface 41$a$, are formed with metal wiring, and are mounted with various metal electronic components. The sensor mounting surface 41$a$ and the sensor non-mounting surface 41$b$ of the substrate 41 are metal surfaces formed by metal bodies.

The antenna 31 is mounted on an antenna mounting surface 42$a$, which is a surface on one side of the flat plate shaped substrate 42. The antenna mounting surface 42a and an antenna non-mounting surface 42b, which is a surface on the other side of the substrate 42 opposite to the antenna mounting surface 42a, are formed with metal wiring, and are mounted with various metal electronic components. The antenna mounting surface 42a and the antenna non-mounting surface 42b of the substrate 42 are metal surfaces formed by metal bodies.

The sensor non-mounting surface 41b on the side opposite to the side mounted with the pressure sensor 14 of the substrate 41 and the antenna mounting surface 42a on the side mounted with the antenna 31 of the substrate 42 face each other. The substrates 41 and 42 are arranged in a stacked manner such that the sensor non-mounting surface 41b and the antenna mounting surface 42a face each other. The substrates 41, 42 are arranged facing each other inside the main body 1 of the sphygmomanometer.

As compared with a conventional sphygmomanometer, the surface area of the substrate becomes larger if the antenna 31 is additionally mounted on a substrate for the conventional sphygmomanometer. If the surface area of the substrate becomes larger, an occupying volume of the substrate in the main body 1 of the sphygmomanometer becomes large, which is not desirable since it enlarges the housing of the main body 1 and increases the cost. In the present embodiment, therefore, the substrate 42 mounted with the antenna 31 of the radio-controlled clock 13 is separated from the substrate 41 serving as a main substrate mounted with devices that configure the sphygmomanometer such as the pressure sensor 14.

The substrate 42 including the antenna 31 is separated from the substrate 41. Furthermore, the substrates 41, 42 are not arranged on the same plane, and are arranged in a stacked manner so as to face each other. The substrate 41 is arranged inclined with respect to the substrate 42, and the substrate 42 is arranged in a space formed at the lower side of the sensor non-mounting surface 41b of the substrate 41 due to the inclination of the substrate 41. The substrate 41 and the substrate 42 are arranged such that a center line CL2, which is an axis line of the pump 16, to be described later, comes between the substrates 41, 42. The occupying volume of the substrates 41, 42 in the main body 1 thus can be reduced, and hence, the housing of the main body 1 can be miniaturized and the entire sphygmomanometer can be miniaturized.

Furthermore, the substrate 42 mounted with the antenna 31 can be arranged parallel to an installing surface where the sphygmomanometer is installed regardless of the mounting angle of the substrate 41, which is the main substrate, inside the housing of the main body 1 of the sphygmomanometer. If the installing surface is horizontal with respect to the ground, that is, if the sphygmomanometer is mounted on a horizontal surface plate, the substrate 42 can be installed horizontally. The antenna 31 can be horizontally installed by horizontally installing the substrate 42 serving as the second substrate. The standard radio wave transmitting the radio-controlled clock signal is transmitted in horizontal polarized wave. The antenna 31 receiving the standard radio wave has directivity. The antenna 31 is desirably installed horizontally (laterally) with respect to the ground for use to efficiently receive the standard radio wave of horizontal polarized wave. That is, the antenna 31 can satisfactorily receive the standard radio wave, and the reception performance of the standard radio wave by the antenna 31 can be more enhanced by installing the substrate 42 horizontally.

Figure 6:
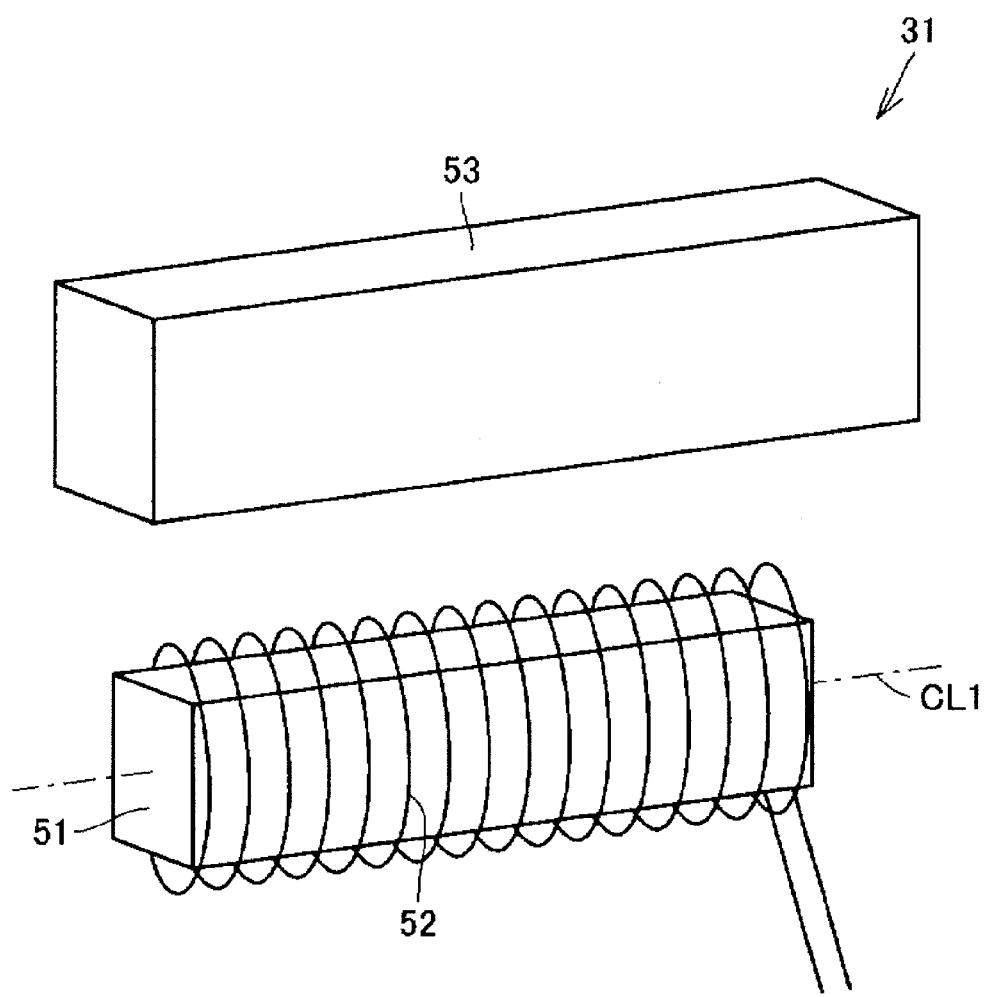
FIG. 6 is an exploded perspective view showing a schematic configuration of an antenna of the radio-controlled clock.

FIG. 6 is an exploded perspective view showing a schematic configuration of the antenna of the radio-controlled clock. As shown in FIG. 6, the antenna 31 includes a bar-shaped core 51 made from a magnetic body such as amorphous metal or ferrite having satisfactory radio wave reception sensitivity, and a coil 52 in which a copper line having its surface insulation-coated is wound around the periphery of the core 51. The core 51 functions as a shaft of the antenna 31. The core 51 and the coil 52 are included in the antenna structural body. The antenna 31 includes an antenna case 53 that covers the core 51 and the coil 52. The antenna structural body is fixed to the antenna mounting surface 42a of the substrate 42 while being accommodated inside the antenna case 53.

The core 51 has a longitudinal direction, where the shape of a traverse surface orthogonal to the longitudinal direction is formed in a square shape, as shown in FIG. 6. A line connecting the center points of the traverse surfaces at both ends in the longitudinal direction of the square bar-shaped core 51 forms a center line CL1 of the core 51. The center line CL1 indicates the extending direction of the core 51. The traverse surface of the core 51 is not limited to a square, and may be formed in other shapes such as a circle or an ellipse.

Figure 7:
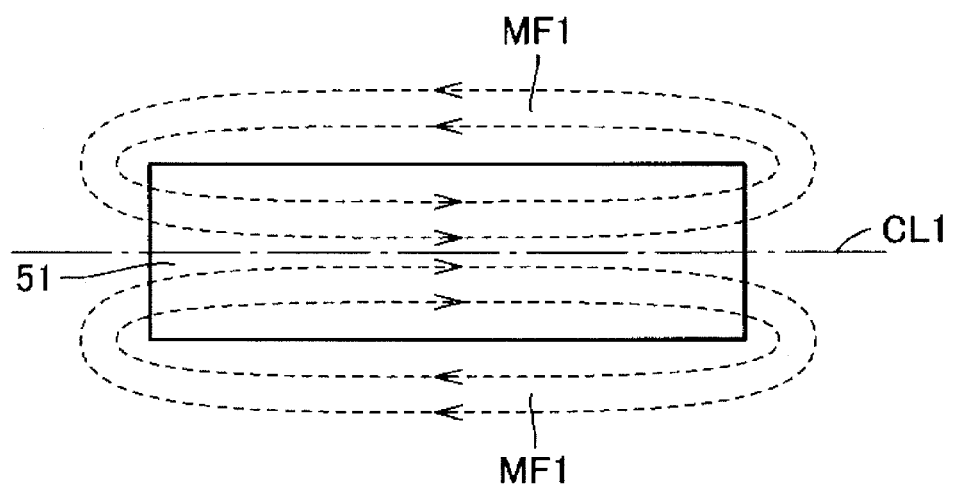
FIG. 7 is a schematic view showing a magnetic field at a periphery of a core of the radio-controlled clock.

FIG. 7 is a schematic view showing a magnetic field at the periphery of the core of the radio-controlled clock. When the magnetic field MF1 shown in FIG. 7 passes the interior of the core 51, an electromotive force by electromagnetic induction is generated, and the energy of the magnetic field is converted as a current by the coil 52 shown in FIG. 6. In FIG. 7, the illustration of the coil 52 is omitted for simplification.

If a metal body substantially orthogonal in the direction of the magnetic line of force indicating the magnetic field MF1 around the bar-shaped core 51 shown in FIG. 7 is arranged at the periphery of the core 51, the magnetic field MF1 is shielded by the metal body. For example, if the substrate 41 is orthogonal to the substrate 42 and the sensor mounting surface 41a or the sensor non-mounting surface 41b is arranged as a vertical surface with respect to the antenna mounting surface 42, the magnetic field MF1 is shielded since the metal surface of the substrate 41 becomes a shield, and the magnetic field MF1 is disturbed. The input value of the standard radio wave lowers when the magnetic field MF1 on the antenna 31 side is disturbed, which may cause lowering in reception sensitivity.

In the present embodiment, therefore, the substrate 42 mounted with the antenna 31 and the other substrate 41 are arranged such that the sensor non-mounting surface 41b faces the antenna mounting surface 42a of the substrate 42 and a predetermined spacing is formed between the sensor non-mounting surface 41b and the antenna mounting surface 42a. The substrates 41, 42 are arranged such that the magnetic field MF1 around the core 51 is suppressed from being shielded by the metal surface formed on the surface of the substrate 41. The influence of the metal surface of the substrate 41 and the shield case 43 of the pressure sensor 14 on the antenna 31 mounted on the substrate 42 is thereby alleviated, and the magnetic field MF1 can be suppressed from being shielded by the metal body such as the substrate 41 or the shield case 43. Therefore, the reception performance of the standard radio wave by the antenna 31 can be suppressed from lowering.

Figure 8:
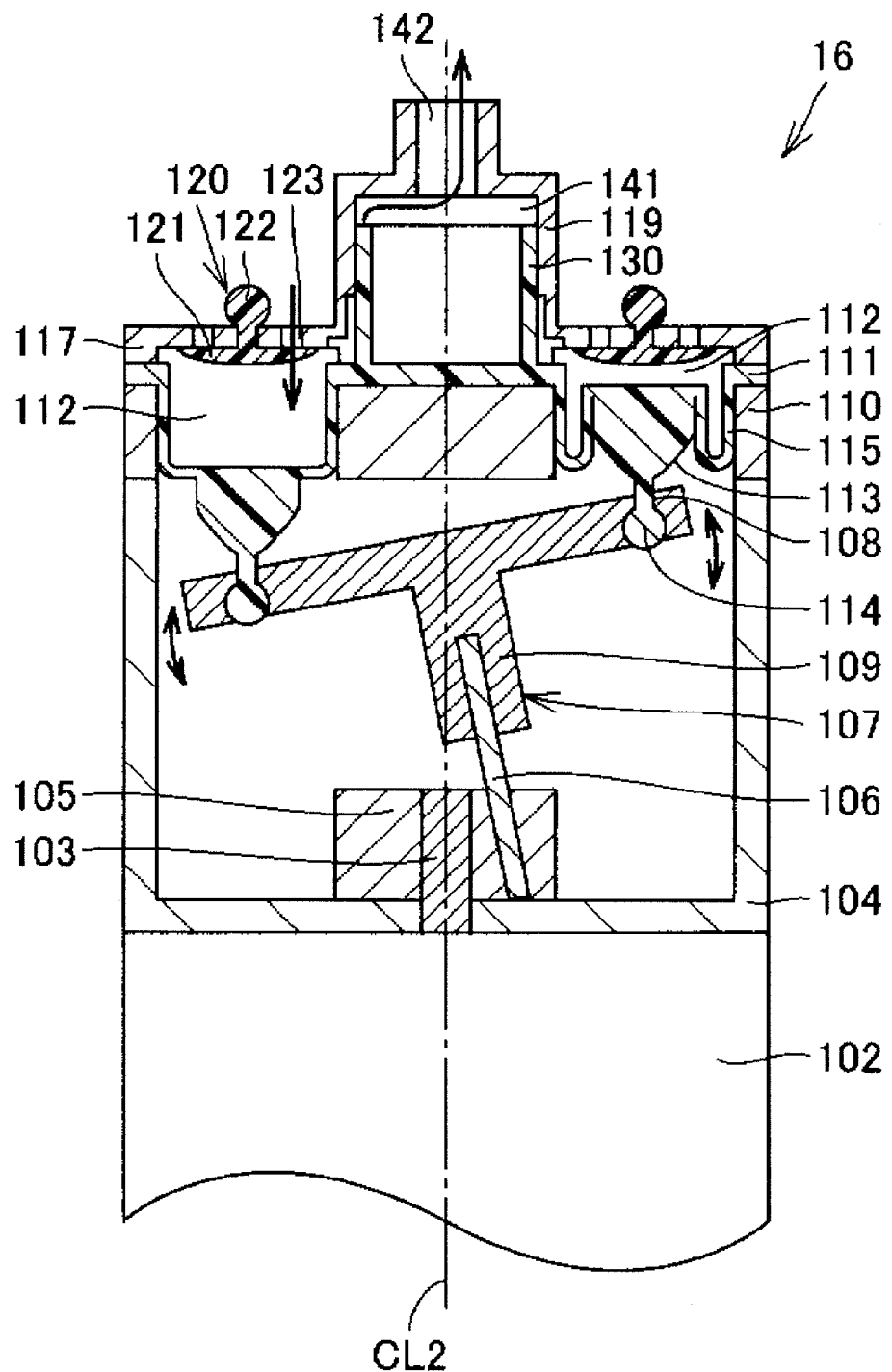
FIG. 8 is a cross-sectional schematic view showing a schematic configuration of a pump.

FIG. 8 is a cross-sectional schematic view showing a schematic configuration of a pump. As shown in FIG. 8, the pump 16 is a diaphragm pump that includes a rubber-like diaphragm forming a pump chamber in the case, and that transports gas by change in volume of the pump chamber. A motor 102, which is a small DC motor, is arranged at the lower part of the pump 16. The motor 102 is attached with an output shaft 103 that rotates by the rotational movement of the motor 102. The output shaft 103 is extended to the interior of the lower case 104 of the pump 16. The output shaft 103 is extended in the vertical direction.

A rotating body 105 is fixed at the end of the output shaft 103. The rotating body 105 rotationally moves integrally with the output shaft 103. A drive shaft 106 is fixed to the rotation body 105. A basal end of the drive shaft 106, which is one end fixed to the rotating body 105, is positioned away from an extended line of the center of rotation of the output shaft 103. The other end of the drive shaft 106 has the extended line of the center axis intersecting the extended line of the center of rotation of the output shaft 103. The drive shaft 106 is thus inclined with respect to the output shaft 103. The drive shaft 106 is extended in a direction inclined with respect to the vertical direction.

A driving body 107 is rotatably inserted on the distal end side of the drive shaft 106. The driving body 107 has a planar shape formed in a circular shape. The driving body 107 includes three through holes 108 formed at an interval of 120° from each other. A tubular supporting portion 109 extending in the extending direction of the drive shaft 106 is formed at the lower side of the driving body 107, and the distal end of the drive shaft 106 is rotatably inserted to a hole formed at the middle of the supporting portion 109. An upper case 110 is installed at the upper part of the lower case 104. The upper case 110 is fixed to the upper end of the lower case 104 at the lower end thereof with a screw-in action, and the like.

A diaphragm main body 111 is arranged at the upper side of the upper case 110. The diaphragm main body 111 is formed by an elastic material or the like, such as a soft and thin rubber, and is formed in a circular plate shape. Pump chambers 112 formed at an equal angular interval of 120° are formed at the lower side of the diaphragm main body 111. The upper case 110 is arranged to surround the periphery of the pump chambers 112.

A bell-shaped drive unit 113 is arranged at the lower side of the pump chamber 112. A head 114 is formed at the distal end of the drive unit 113 with a narrow neck interposed therebetween. The diaphragm main body 111 is assembled to the driving body 107 such that the head 114 is passed through a through-hole 108 formed in the driving body 107, and the neck is arranged to be positioned inside the through-hole 108. A diaphragm unit 115 of thin film form arranged in a freely stretchable manner is attached to the outer peripheral part of the drive unit 113. The diaphragm unit 115 air tightly couples the diaphragm main body 111 forming the peripheral edge of the circular plan shape of the pump chamber 112 and the outer peripheral part of the drive unit 113.

A valve housing 117 for covering the pump chamber 112 from the upper side and closing the pump chamber 112 is arranged on the upper side of the diaphragm main body 111. The pump chamber 112 is formed to be surrounded by the drive unit 113, the diaphragm unit 115, the diaphragm main body 111, and the valve housing 117.

A gas collecting body 119 is arranged further on the upper side of the valve housing 117. An umbrella valve 120 is installed on the upper side of the valve housing 117. The umbrella valve 120 includes a valve main body 121 and a head 122. The umbrella valve 120 is assembled to the valve housing 117 by passing the head 122 through the through-hole formed in the valve housing 117. The umbrella valve 120 functions as a check valve that allows the flow of air towards the interior of the pump chamber 112 and prohibits the flow in the opposite direction.

A discharge valve 130 is formed to extend to the upper side along the wall surface of the gas collecting body 119 from the diaphragm main body 111. The discharge valve 130 functions as a check valve that allows the flow of air discharged to the outside from the pump chamber 112 and prohibits the flow in the opposite direction. The air transported by the pump 16 flows from an exhaust portion 142 to the outside through an air chamber 141 formed inside the gas collecting body 119.

The space surrounded by the lower case 104, the upper case 110, and the diaphragm main body 111 forms an internal space of the pump 16. An air intake path communicating the internal space of the pump 16 and the exterior of the pump 16 is formed at one area or a plurality of areas in at least one of the lower case 104 or the upper case 110. The air flows from the outside into the interior space of the pump 16 through the air intake path.

The diaphragm main body 111 and the drive unit 113 are air tightly coupled by the diaphragm unit 115 of thin film form. The interior space of the pump 16 and the pump chamber 112 are thus separate spaces. The pump chamber 112 is formed to a structure of communicating to the external space of the pump 16 through a ventilation path formed in the valve housing 117 only when the valve body 121 of the umbrella valve 120 is separated from the valve housing 117 and the umbrella valve 120 is in the open state.

Figure 9:
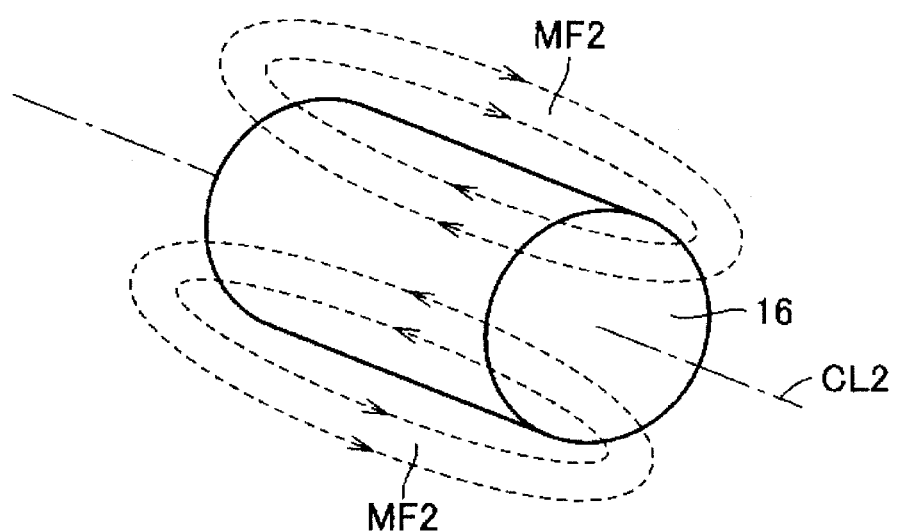
FIG. 9 is a schematic view showing a magnetic field of a periphery of the pump.

FIG. 8 shows the center line CL2 that is the axis line of the output shaft 103 (i.e., axis line of motor 102) with a dashed dotted line. When the motor 102, which functions as an actuator for operating the pump 16, rotates about the center line CL2, a magnetic field MF2 that passes the interior of the pump 16 in the direction along the center line CL2 is formed, as shown in FIG. 9. FIG. 9 is a schematic view showing the magnetic field of the periphery of the pump.

As shown in FIG. 4, the antenna 31 and the pump 16 are arranged so that the center line CL1 of the core 51 of the antenna 31 of the radio-controlled clock and the center line CL2 of the pump 16 become orthogonal. The substrate 42 mounted with the antenna 31 is installed so that the core 51 is arranged perpendicularly with respect to the output shaft 103 of the pump 16. With such an arrangement, the magnetic field MF2 generated by the drive of the pump 16 can be prevented from interfering the magnetic field MF1 at the periphery of the core 51. That is, the magnetic field MF2 can be suppressed from influencing the magnetic field MF1 and causing disturbance in the magnetic field MF1. Since the magnetic field MF1 is suppressed from being interfered by the pump 16, the lowering in the reception performance of the standard radio wave by the antenna 31 can be suppressed.

Second Embodiment

Figure 10:
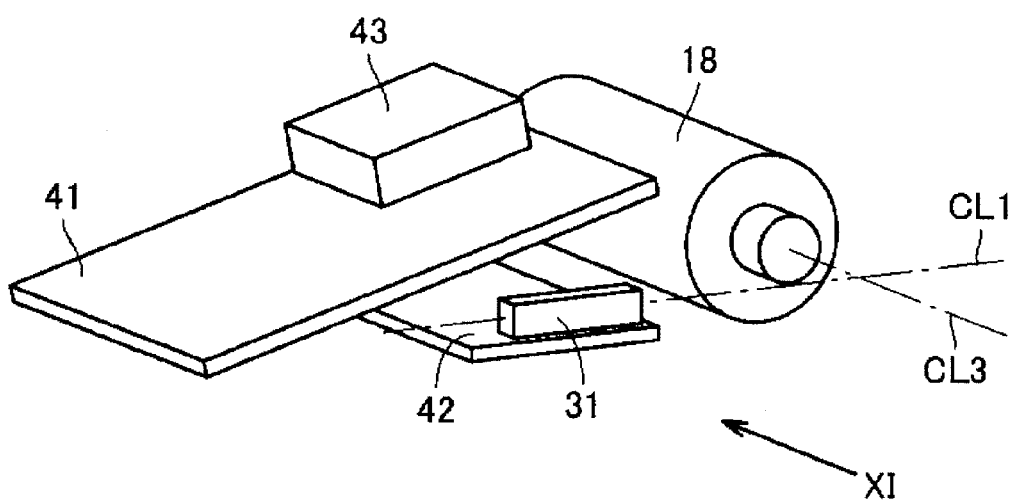
FIG. 10 is a perspective view showing an arrangement of each device mounted in a main body of a sphygmomanometer according to a second embodiment.
Figure 11:
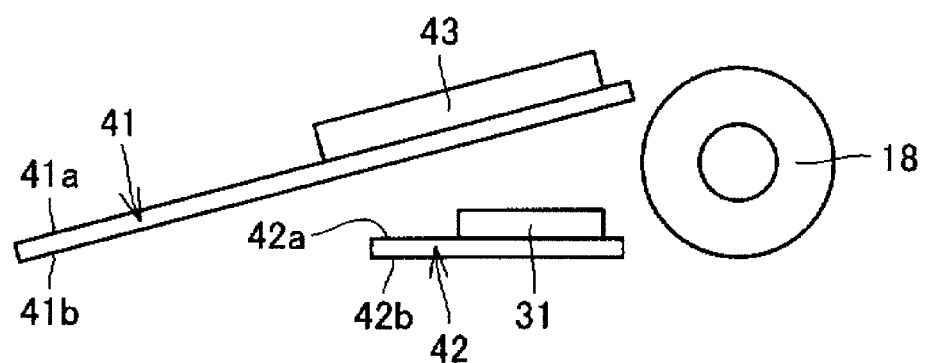
FIG. 11 is a side view of each device shown in FIG. 10 when seen from the direction of the arrow XI in FIG. 10.

FIG. 10 is a perspective view showing an arrangement of each device mounted in a main body of a sphygmomanometer according to a second embodiment. FIG. 11 is a side view of each device shown in FIG. 10 when seen from the direction of the arrow XI in FIG. 10. In the second embodiment, the arrangement of the valve 18 with respect to the substrates 41, 42 in the main body 1 of the sphygmomanometer is specified in place of the pump 16 described in the first embodiment.

Figure 12:
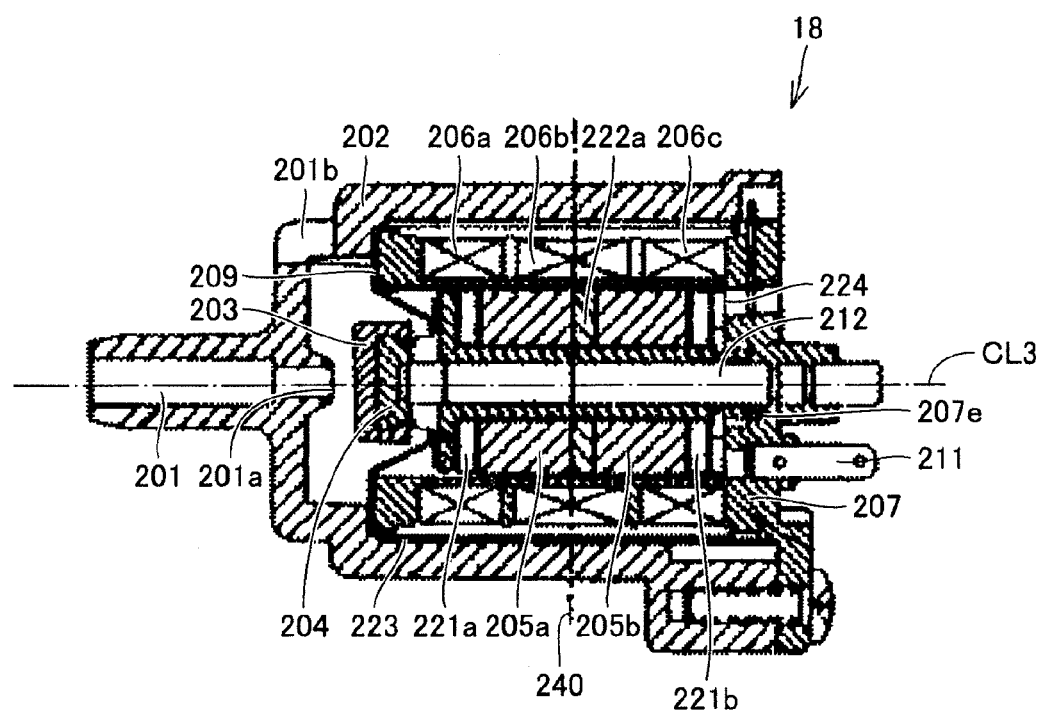
FIG. 12 is a cross-sectional schematic view showing a schematic configuration of a valve.

FIG. 12 is a cross-sectional schematic view showing the schematic configuration of the valve. As shown in FIG. 12, the valve 18 is a flow rate control valve used to control the gas flow rate discharged from the air bag 21 of the cuff 2 in the sphygmomanometer and gradually lower the pressure in the air bag 21. The flow rate control valve is an electromagnetic drive valve that uses two permanent magnets 205a, 205b and three electromagnetic coils 206a, 206b, 206c, where a housing is configured at the back part of the frame case 202 and the bobbin 207. The housing (frame case 202) is formed with a gas flow-in port 201a where a nozzle-shaped inner tube 201 opens to the inside, and a plurality of (three herein) gas flow-out ports 201b communicating to the gas flow-in port 201a by an internal space.

In the housing, a hollow operation shaft (movable member) 204 is arranged to move forward and backward with respect to the gas flow-in port 201a, and an orifice gasket (open/close member) 203 is attached to the distal end of the operation shaft 204 opposing the gas flow-in port 201a so as to open and close the gas flow-in port 201a with the movement of the operation shaft 204.

A fixed shaft 212 of a non-magnetic body is inserted to the hollow part inside the operation shaft 204, and the bobbin 207 is integrally fixed to the fixed shaft 212. Permanent magnets 205a, 205b, a yoke 222a, and elastic bodies 221a, 221b are fixed at the outer periphery of the operation shaft 204 with a retaining ring 224. Therefore, the operation shaft 204 integrally moves with the permanent magnets 205a, 205b, the yoke 222a, and the like, and is movable in a range the orifice gasket 203 hits the gas flow-in port 201a and completely closes the gas flow-in port 201a and until the back end of the operation shaft 204 hits a stopper 207e arranged in the bobbin 207, and linearly moves along the fixed shaft 212.

The elastic body 221a arranged facing the end face of the permanent magnet 205a is sandwiched by the operation shaft 204 and the permanent magnet 205a, and the elastic body 221b arranged facing the end face of the permanent magnet 205b is sandwiched by the retaining ring 224 and the permanent magnet 205b herein. The bobbin 207 is arranged at the periphery of the permanent magnets 205a, 205b, and three electromagnetic coils 206a, 206b, 206c are arranged in the bobbin 207.

In each electromagnetic coil 206a, 206b, 206c, the winding direction is set such that the operation shaft 204 receives the synthetic force of the electromagnetic forces by each electromagnetic coil 206a, 206b, 206c and each permanent magnet 205a, 205b in the movement direction. Specifically, the electromagnetic coils are respectively arranged in the bobbin 207 such that the winding direction of the electromagnetic coil 206 in the middle is the right rotation, the winding direction of the electromagnetic coils 206a, 206c is the left rotation, so that the winding direction alternately becomes opposite. That is, the current flows in the direction opposite to the electromagnetic coil 206b in the electromagnetic coils 206a, 206c adjacent to the electromagnetic coil 206b. The electromagnetic coils 206a, 206b, and 206c are connected to an external terminal 211.

The permanent magnets 205a, 205b are arranged substantially equally to the left and the right with respect to a central part 240 of the middle electromagnetic coil 206b. A yoke 223 is arranged at the periphery of three electromagnetic coils 206a, 206b, 206c, and the electromagnetic coils 206a, 206b, 206c, the permanent magnets 205a, 205b, the operation shaft 204, and the fixed shaft 212 are positioned on the inner side of the cylindrical yoke 223. The operation shaft 204 is coupled to the frame case 202 by a damper 209, and is biased in the right direction in FIG. 12 by the spring action of the damper 209.

The operation of the flow rate control valve configured as above will now be described. The electromagnetic force is generated by each electromagnetic coil 206a, 206b, 206c and each permanent magnet 205a, 205b by flowing a current of a predetermined value from the external terminal 211 to the electromagnetic coils 206a, 206b, 206c, and a thrust force in the left direction in FIG. 12 is acted on the permanent magnets 205a, 205b using repulsion and attraction of the magnetic poles of the permanent magnets 205a, 205b and the electromagnetic coils 206a, 206b, 206c.

Figure 13:
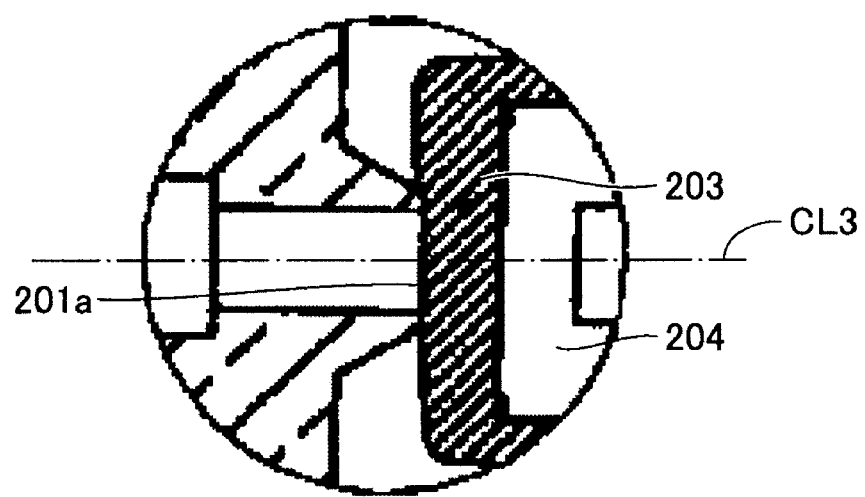
FIG. 13 is a partially enlarged cross-sectional view showing a state in which a gas flow-in port is completely closed.

The operation shaft 204 attached with the permanent magnets 205a, 205b strongly moves in the left direction in FIG. 12 by the thrust force while overcoming the repulsion force of the damper 209, whereby the orifice gasket 203 contacts the gas flow-in port 201a so that the inner tube 201 is in a completely closed state, as shown in FIG. 13. FIG. 13 is a partially enlarged cross-sectional view showing a state in which the gas flow-in port is completely closed.

Figure 14:
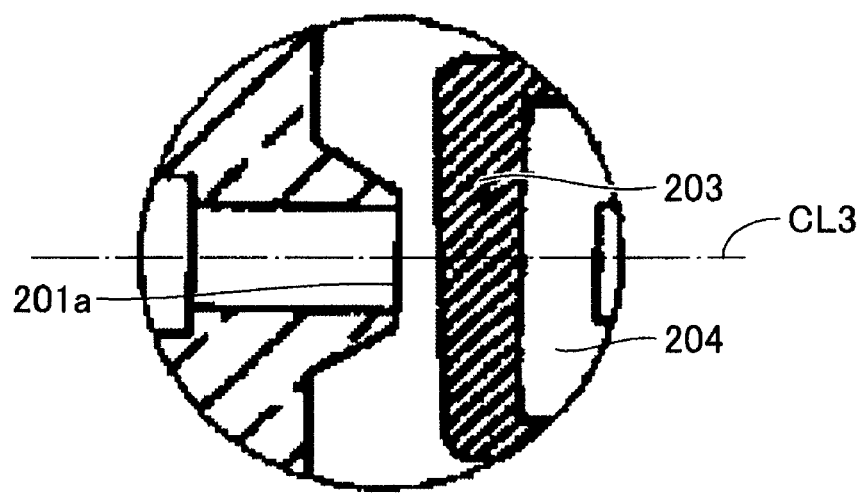
FIG. 14 is a partially enlarged cross-sectional view showing a state in which the gas flow-in port is completely opened.

When the supply current to the electromagnetic coils 206a, 206b, 206c is gradually reduced after the closed state of the inner tube 201, the electromagnetic force gradually weakens according to the current. The thrust force received by the permanent magnets 205a, 205b thus lowers, the operation shaft 204 gradually moves in the right direction in FIG. 12 by the elastic force of the damper 209, and the orifice gasket 203 slowly moves away from the gas flow-in port 201a. As a result, the gas flow-in port 201a is microscopically and continuously opened, and eventually becomes a completely opened state, as shown in FIG. 14. FIG. 14 is a partially enlarged cross-sectional view showing a state in which the gas flow-in port is completely opened.

The orifice gasket 203 is attached to the distal end of the operation shaft 204, and reciprocates in the left and right direction in FIG. 12 to FIG. 14, which is the axis line direction the operation shaft 204 extends, along with the operation shaft 204. The orifice gasket 203 causes the valve 18 to be in the closed state by coming into contact with the gas flow-in port 201a, and causes the valve 18 to be in the opened state by moving away from the gas flow-in port 201a. The orifice gasket 203 functions as a valve body of the valve 18.

The center line CL3 of the valve 18 that is the axis line of the fixed shaft 212 is shown with a dashed dotted line in FIG. 12. The center line CL3 indicates the reciprocating direction of the orifice gasket 203 that is the valve body of the valve 18. The permanent magnets 205a, 205b and the electromagnetic coils 206a, 206b, 206c are installed about the center axis CL3 inside the valve 18 that is the electromagnetic drive valve. Thus, the magnetic field that passes the interior of the valve 18 in the direction along the center line CL3 is formed. Similar to the pump 16 shown in FIG. 9, the direction of the magnetic field generated by the valve 18 is the direction that passes the interior of the valve 18 along the center line CL3.

As shown in FIG. 10, the antenna 31 and the valve 18 are arranged so that the center line CL1 of the core 51 of the antenna 31 of the radio-controlled clock and the center line CL3 of the valve 18 become orthogonal. The substrate 42 mounted with the antenna 31 is installed so that the core 51 is arranged perpendicularly with respect to the fixed shaft 212 of the valve 18. With such an arrangement, the magnetic field can be suppressed from interfering with the magnetic field MF1 at the periphery of the core 51 and causing disturbance in the magnetic field MF1. Since the magnetic field MF1 can be suppressed from being interfered by the valve 18, the lowering in the reception performance of the standard radio wave by the antenna 31 can be suppressed.

Third Embodiment

Figure 15:
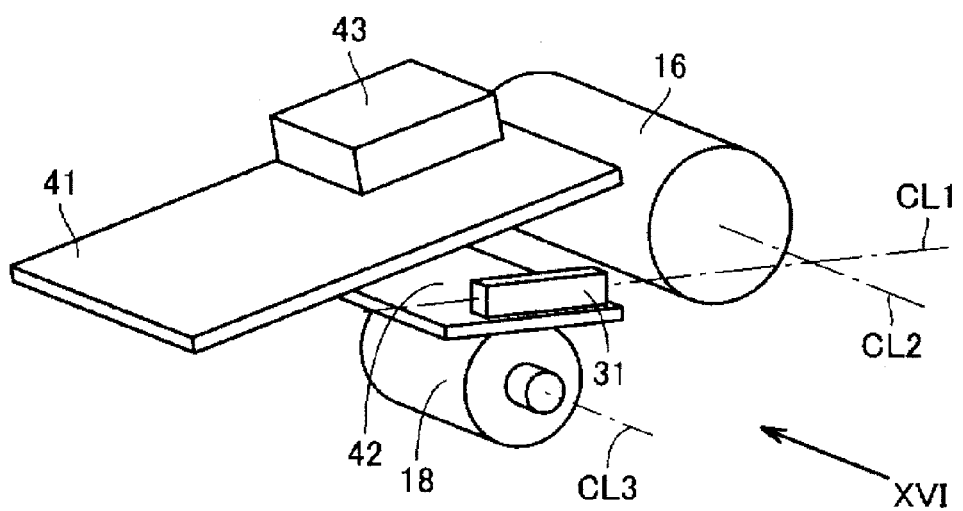
FIG. 15 is a perspective view showing an arrangement of each device mounted in a main body of a sphygmomanometer according to a third embodiment.
Figure 16:
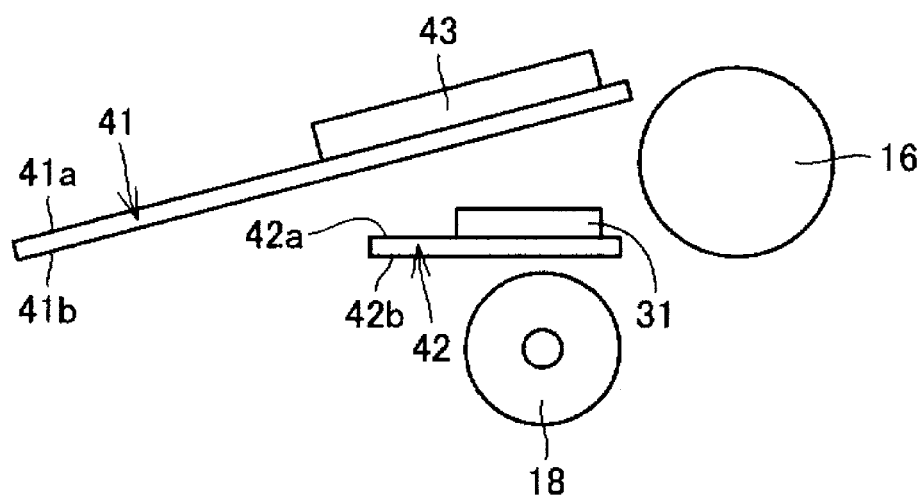
FIG. 16 is a side view of each device shown in FIG. 15 when seen from the direction of the arrow XVI in FIG. 15.

FIG. 15 is a perspective view showing an arrangement of each device mounted in a main body of a sphygmomanometer according to a third embodiment. FIG. 16 is a side view of each device shown in FIG. 15 when seen from the direction of the arrow XVI in FIG. 15. In the third embodiment, the arrangement of the valve 18 with respect to the substrates 41, 42 in the main body 1 of the sphygmomanometer is specified in addition to the arrangement of each device described in the first embodiment.

As shown in FIG. 15 and FIG. 16, the valve 18 is arranged with the substrate 42 serving as a second substrate interposed with respect to the antenna 31. The substrate 42 is interposed between the valve 18 and the antenna 31. The valve 18 is installed on the lower side of the substrate 42. The valve 18 is arranged to face the antenna non-mounting surface 42b on the side opposite to the antenna mounting surface 42a of the substrate 42. The valve 18 is arranged so that the center line CL3 of the valve is parallel to the substrate 42. By defining the arrangement of the valve 18 and the antenna 31 in this manner, the antenna 31 is shielded from the magnetic field formed when the valve 18 is driven by the metal surface of the antenna non-mounting surface 42b of the substrate 42. Therefore, interference to the magnetic field MF1 about the antenna 31 can be further suppressed.

Similar to the first and second embodiments, the antenna 31, the pump 16, and the valve 18 are arranged so that the center line CL1 of the core 51 indicating the extending direction of the antenna 31 and the center line CL2 of the pump 16 become orthogonal and the center line CL1 and the center line CL3 of the valve 18 become orthogonal. Therefore, the magnetic field generated by the drive of the pump 16 and the drive of the valve 18 can be suppressed from interfering with the magnetic field MF1 at the periphery of the core 51 and causing disturbance in the magnetic field MF1. Since the magnetic field MF1 is suppressed from being interfered by the pump 16 and the valve 18, the lowering in the reception performance of the standard radio wave by the antenna 31 can be suppressed.

Fourth Embodiment

Figure 17:
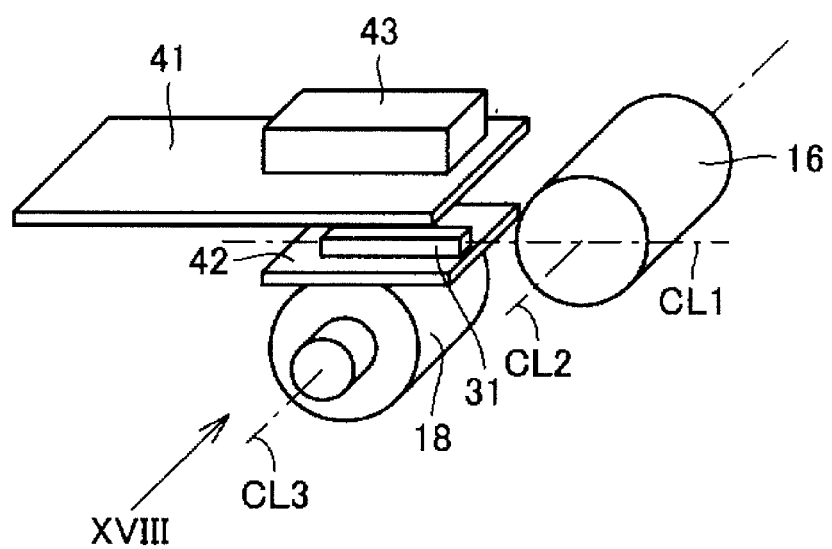
FIG. 17 is a perspective view showing an arrangement of each device mounted in a main body of a sphygmomanometer according to a fourth embodiment.
Figure 18:
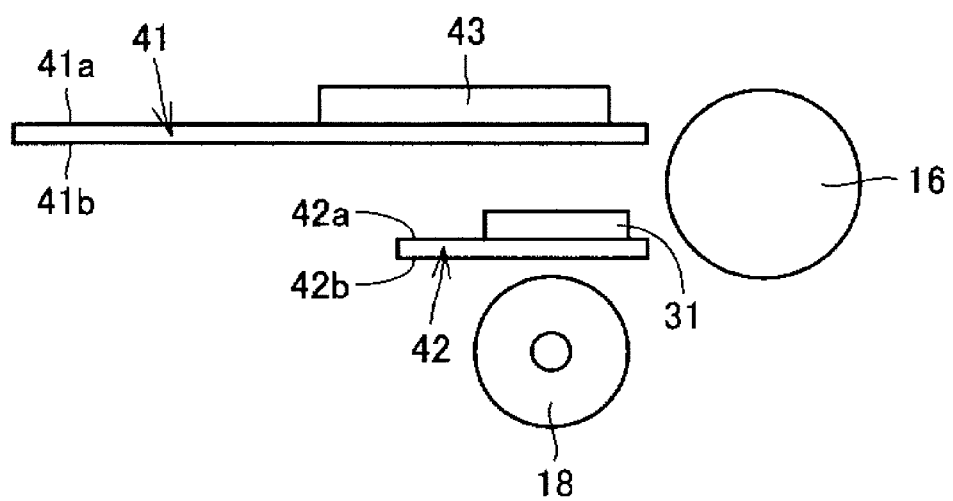
FIG. 18 is a side view of each device shown in FIG. 17 when seen from the direction of the arrow XVIII in FIG. 17.

FIG. 17 is a perspective view showing an arrangement of each device mounted in the main body of the sphygmomanometer according to a fourth embodiment. FIG. 18 is a side view of each device shown in FIG. 17 when seen from the direction of the arrow XVIII in FIG. 17. In the fourth embodiment, the arrangement of the substrates 41, 42 is different from the third embodiment, and specifically, the substrate 41 and the substrate 42 are installed in parallel.

Even if the substrates 41, 42 are installed so as to be parallel, the substrate 42 mounted with the antenna 31 and the other substrate 41 are arranged so that the sensor non-mounting surface 41b faces the antenna mounting surface 42a of the substrate 42, and a predetermined spacing forms between the sensor non-mounting surface 41b and the antenna mounting surface 42a. The substrates 41, 42 are arranged such that the magnetic field MF1 about the core 51 is suppressed by being shielded by the metal surface formed on the surface of the substrate 41. Therefore, the magnetic field MF1 can be suppressed from being shielded by the substrate 41, and hence the lowering of the reception performance of the standard radio wave by the antenna 31 can be suppressed.

The substrates 41, 42 may be arranged inclined with respect to each other as described in the first embodiment or may be arranged in parallel as described in the present embodiment, in correspondence with the space in the main body 1. The housing of the main body 1 can be further miniaturized and the entire sphygmomanometer can be further miniaturized by arranging the substrates 41, 42 so as to further reduce the occupying volume of the substrates 41, 42 in the main body 1.

Fifth Embodiment

Figure 19:
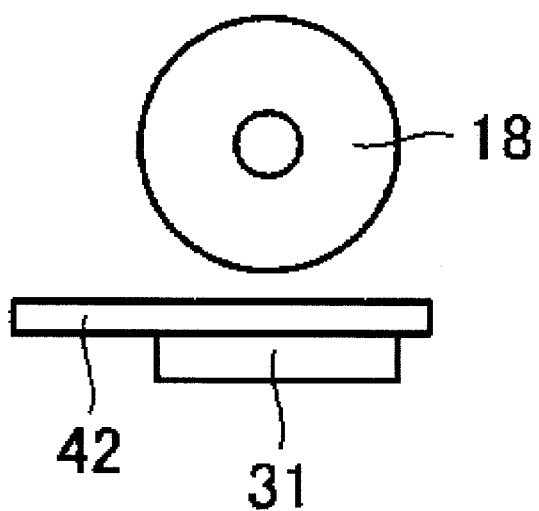
FIG. 19 is a perspective view showing an arrangement of each device mounted in a main body of a sphygmomanometer according to a fifth embodiment.

FIG. 19 is a perspective view showing an arrangement of each device mounted in the main body of the sphygmomanometer according to a fifth embodiment. In FIG. 19, only the substrate 42 mounted with the antenna 31 and the valve 18 are illustrated, and the illustration of the substrate 41 and the pump 16 is omitted. The fifth embodiment differs from the third and fourth embodiments in that the valve 18 is installed on the upper side of the substrate 42, but is similar to the third and fourth embodiments in that the valve 18 is arranged with the substrate 42 interposed with respect to the antenna 31, and the substrate 42 is interposed between the valve 18 and the antenna 31.

By defining the arrangement of the valve 18 and the antenna 31 in this manner, similar to the third and fourth embodiments, the antenna 31 is shielded from the magnetic field which is formed when the valve 18 is driven by the metal surface of the antenna non-mounting surface 42b of the substrate 42. Therefore, interference to the magnetic field MF1 about the antenna 31 can be further suppressed.

The embodiments of the present invention have been described above, but the configurations of each embodiment may be appropriately combined. The embodiments disclosed herein are illustrative in all aspects and should not be construed as being restrictive. The scope of the invention is defined by the claims rather than by the description made above, and all modifications equivalent in meaning with the claims and within the scope thereof are intended to be encompassed therein.

DESCRIPTION OF SYMBOLS 1 main body
2 cuff
3 air tube
4 display unit
13 radio-controlled clock
14 pressure sensor
16 pump
18 valve
19 valve drive circuit
20 CPU
21 air bag
26 band
27 surface fastener
31 antenna
32 reception circuit
33 clock signal analyzing circuit
41, 42 substrate
41a sensor mounting surface
41b sensor non-mounting surface
42a antenna mounting surface
42b antenna non-mounting surface
43 shield case
51 core
52 coil
53 antenna case
CL1, CL2, CL3 center line
MF1, MF2 magnetic field

The invention claimed is:
1. A blood pressure measurement device comprising:
a cuff, which is configured to be attached to a blood pressure measurement site of a person to be measured and which includes a gas bag filled with gas;
a pump for transferring gas to the gas bag;
a flow rate control valve for controlling a gas flow rate discharged from the gas bag;
a pressure sensor for detecting pressure in the gas bag;
a first substrate including a sensor mounting surface and a sensor non-mounting surface, and having the pressure sensor mounted on the sensor mounting surface;

a radio-controlled clock, including an antenna for receiving a standard radio wave including time information, for timing a current time; and a second substrate including an antenna mounting surface and an antenna non-mounting surface, and having the antenna mounted on the antenna mounting surface;

wherein the pump includes a motor that rotates about an axis line and operates the pump, wherein the antenna includes a bar-shaped magnetic body core and a coil wound around the magnetic body core, wherein the pump is arranged such that an axis line direction of the motor and an extending direction of the magnetic body core are substantially orthogonal; and wherein the first substrate and the second substrate are arranged so that the sensor non-mounting surface and the antenna mounting surface face each other, or so that the sensor mounting surface and the antenna non-mounting surface face each other.

2. The blood pressure measurement device according to claim 1, wherein the second substrate is arranged parallel to an installing surface where the blood pressure measurement device is installed.

3. The blood pressure measurement device according to claim 1, wherein the first substrate is arranged inclined with respect to the second substrate.

4. The blood pressure measurement device according to claim 1, wherein the first substrate and the second substrate are arranged in parallel.

5. The blood pressure measurement device according to claim 1, wherein the flow rate control valve is an electromagnetic drive valve; and wherein the device is arranged such that a direction of a magnetic field generated by the electromagnetic drive valve and the extending direction of the magnetic body core are orthogonal.

6. The blood pressure measurement device according to claim 1, wherein the second substrate is interposed between the flow rate control valve and the antenna; and wherein the flow rate control valve is installed so that the antenna non-mounting surface and the flow rate control valve face each other.

* * * * *